(12) United States Patent
Herron

(10) Patent No.: US 6,215,300 B1
(45) Date of Patent: Apr. 10, 2001

(54) EDDY CURRENT WIDE PROBE

(75) Inventor: William Lee Herron, Greer, SC (US)

(73) Assignee: General Electric Co., Schenectady, NY (US)

( * ) Notice: Subject to any disclaimer, the term of this patent is extended or adjusted under 35 U.S.C. 154(b) by 0 days.

(21) Appl. No.: 09/231,881

(22) Filed: Jan. 14, 1999

(51) Int. Cl.⁷ .......................... G01N 27/82; G01R 33/12
(52) U.S. Cl. .......................... 324/242; 324/238; 324/240
(58) Field of Search .................... 324/239, 240, 324/241, 242, 243, 228, 232, 234, 236, 237, 238

(56) References Cited

U.S. PATENT DOCUMENTS 4,719,422 * 1/1988 DeWalle et al. ..................... 324/238
6,114,849 * 9/2000 Price et al. ............................ 324/240

* cited by examiner

Primary Examiner—Christine Oda
Assistant Examiner—Henry S. Andersen
(74) Attorney, Agent, or Firm—Nixon & Vanderhye

(57) ABSTRACT

An eddy current probe is configured with one axis of the electrical coil elongated to span a much larger distance than that of conventional coils. Thus, a single pass of the elongated coil can inspect a path of up to 100 times wider than the conventional coil. The parts of the eddy current probe include a pair of elongated ferrite cores disposed end-to-end in a housing block. A pair of receive coils are disposed in the housing block respectively surrounding the elongated ferrite cores. A transmit coil is wound around the receive coils in the housing block, and a pair of ferrite shields are disposed in the housing block sandwiching the transmit coil, the pair of receive coils, and the pair of elongated ferrite cores.

10 Claims, 5 Drawing Sheets

EDDY CURRENT WIDE PROBE

FIELD OF THE INVENTION

The present invention relates to eddy current probes for detecting flaws in conductive materials and, more particularly, to a wide eddy current probe suited for rapid inspection of axial dovetail or shaped holes.

BACKGROUND OF THE INVENTION

Eddy currents provide a measurable indicator of flaws in the surface and sub-surface of conductive materials. They are generally confined to the surface and near surface regions of the material. The eddy currents are affected by changes in the resistivity of the conductive material. Flaws in the material, such as microscopic hairline cracks or pits, affect the localized resistivity of the material. Flaws in a material cause localized variations in the eddy currents in the material. Accordingly, a conductive material can be inspected for flaws by inducing eddy currents in the material.

Eddy current probes detect material flaws by sensing variations in eddy currents. These probes have coils with high-frequency current that project a fluctuating magnetic field into the conductive material being measured. This imposed magnetic field induces eddy currents in the material. The strength of the eddy currents depends on the local resistivity of the material, which resistivity is affected by the presence of material flaws and cracks. The eddy currents create a magnetic field that varies in intensity with the strength and, hence, the presence of material flaws.

The magnetic field created by the eddy currents extends above the material surface up to the probe. The magnetic field from the eddy current induces its own voltage in the probe coil. The eddy magnetic field opposes the coil field. These coupled magnetic fields measurably influence the net current and inductance of the probe coils, and variations in the coil currents vary in response to material flaws and are measured to detect these flaws.

Generally, the current probe is moved axially along the length of the surface to be scanned. As the probe completely traverses each scan line across the surface, the probe is circumferentially indexed to the next scan line around a reference frame. The probe is then drawn in reverse along the next scan line. This scanning and indexing sequence is repeated until the probe completely scans the entire surface. The probe must cover the entire surface to ensure that all material flaws are detected. To do this, the probe travels along straight scan lines parallel to the axis of the surface. If the probe wanders off a scan line, portions of the material surface will be missed, and flaws in the material may escape detection. Moreover, it is difficult to accurately specify the location of flaws when the probe drifts off the intended scan line.

Probe sensitivity to small flaw detection is limited by the size of the probe sense coil. The conventional small probes require long scanning times for scanning and indexing the probe over the entire surface of the part.

DISCLOSURE OF THE INVENTION

If probe sensitivity is not critical for a particular application, it is thus desirable to provide a wider configuration for the eddy current probe to reduce scanning time. According to the present invention, one axis of the electrical coil in the eddy current probe is elongated to span a much larger distance than is true of the conventional coils. Desirably, a single pass of each of the two coils according to the present invention can inspect a path of up to one-half inch width, while to obtain the same coverage, the conventional coil requires up to 50 passes.

According to one aspect of the invention, there is provided an eddy current probe including a housing block, a pair of elongated ferrite cores disposed end-to-end in the housing block along respective longitudinal axes, a pair of receive coils disposed in the housing block respectively surrounding the elongated ferrite cores, a transmit coil wound around the receive coils in the housing block, and a pair of ferrite shields disposed in the housing block. Ferrite shields sandwich the transmit coil, the pair of receive coils and the pair of elongated ferrite cores. The active length of each of the pair of receive coils has been demonstrated as about 0.4". In other embodiments, the housing block is shaped corresponding to a contour of a turbine dovetail. The housing block may be further split axially to allow for part-to-part tolerances. In this context, one of the pair of receive coils is mounted in each half of the housing block.

BRIEF DESCRIPTION OF THE DRAWINGS

These and other aspects and advantages of the present invention will be described in detail with reference to the accompanying drawings, in which.

BEST MODE FOR CARRYING OUT THE INVENTION

The eddy current probe according to the present invention operates in accordance with the principles of conventional eddy current probes, and the details of the operation do not form part of the present invention. Thus, the principles of operation will not be described in detail.

Figure 1:
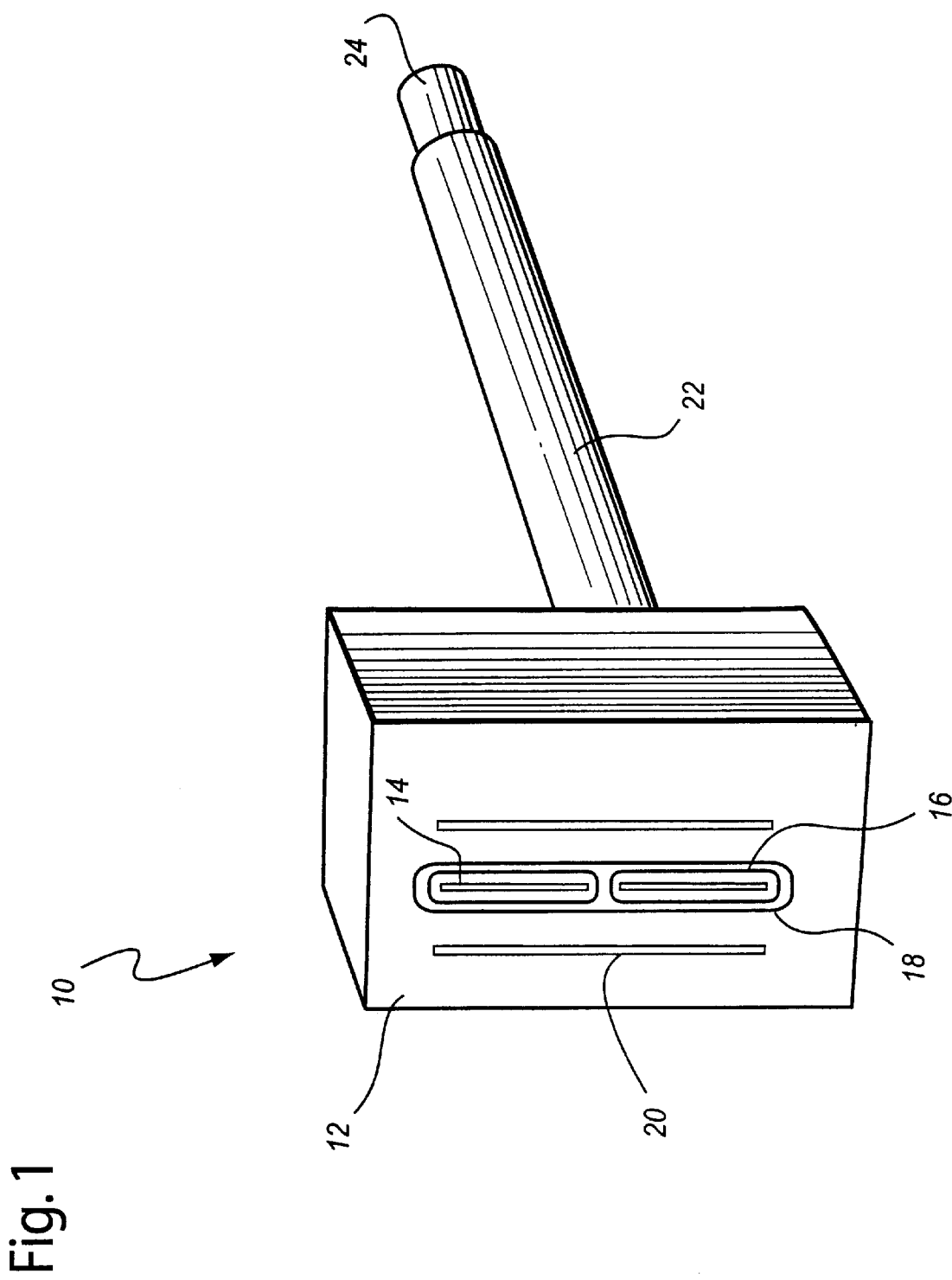
FIG. 1 is a schematic illustration of the eddy current wide probe according to the invention.

In the eddy current probe according to the present invention, one axis of the electrical coil is elongated to span a much larger distance than is true of the conventional coils. With this structure, a single pass of the coil can inspect a path of up to one-half inch width, while to obtain the same coverage, the conventional coil requires up to 50 passes. Referring to FIG. 1, the components of the eddy current probe 10 according to the present invention are disposed in a housing block 12. A pair of elongated ferrite cores 14 are disposed end-to-end in the housing block along respective longitudinal axes thereof. A corresponding pair of receive coils 16 are disposed in the housing block 12, respectively surrounding the elongated ferrite cores 14.

Alternatively, the receive coils may be placed next to one another rather than end-to-end. With the receive coils placed adjacent each other, the effective scan area is decreased by half (i.e., to the length of a single coil, rather than the sum of the lengths of the two coils), but a single flaw will be detected sequentially by each coil, with a consequent increase in overall signal amplitude due to the wiring of the differential coils in the detection bridge. The remaining structure is the same as in the end-to-end receive coil arrangement.

In preferred forms, the probe utilizes differential reflection type coils wired differentially into a bridge circuit for the receive coils 16, but other coil types such as those with lower inspection sensitivity and configured in an absolute configuration could also be used. For example, dual absolute coils could be used, thereby eliminating one of the three coils in the assembly (the excitation or transmit coil), but at the probable cost of some inspection sensitivity. In yet another arrangement, a single absolute coil of the same length as one of the differential coils could be used. This single coil would be wired into a single arm of the instrumentation bridge, with the simplicity coming at the cost of some detection capability. Additionally, thermal compensation that is obtained from having the differential coils essentially adjacent each other would be lost with the single coil.

A transmit coil 18 is wound around the receive coils 16 in the housing block 12. The transmit coil 18 may be wound around each coil separately, thus forming two transmit coils on the same length of wire. A pair of ferrite shields 20 are disposed in the housing block sandwiching the transmit coil 18, the pair of receive coils 16, and a pair of elongated ferrite cores 14.

The eddy current probe 10 also includes a probe stem 22 and a probe electrical connector to instrument cable 24. The probe stem 22 houses the probe electrical connector 24, which connector engages a suitable eddy current instrument providing the excitation signal and the receive coil signal detection, recording and/or analyzing apparatus.

Figure 2:
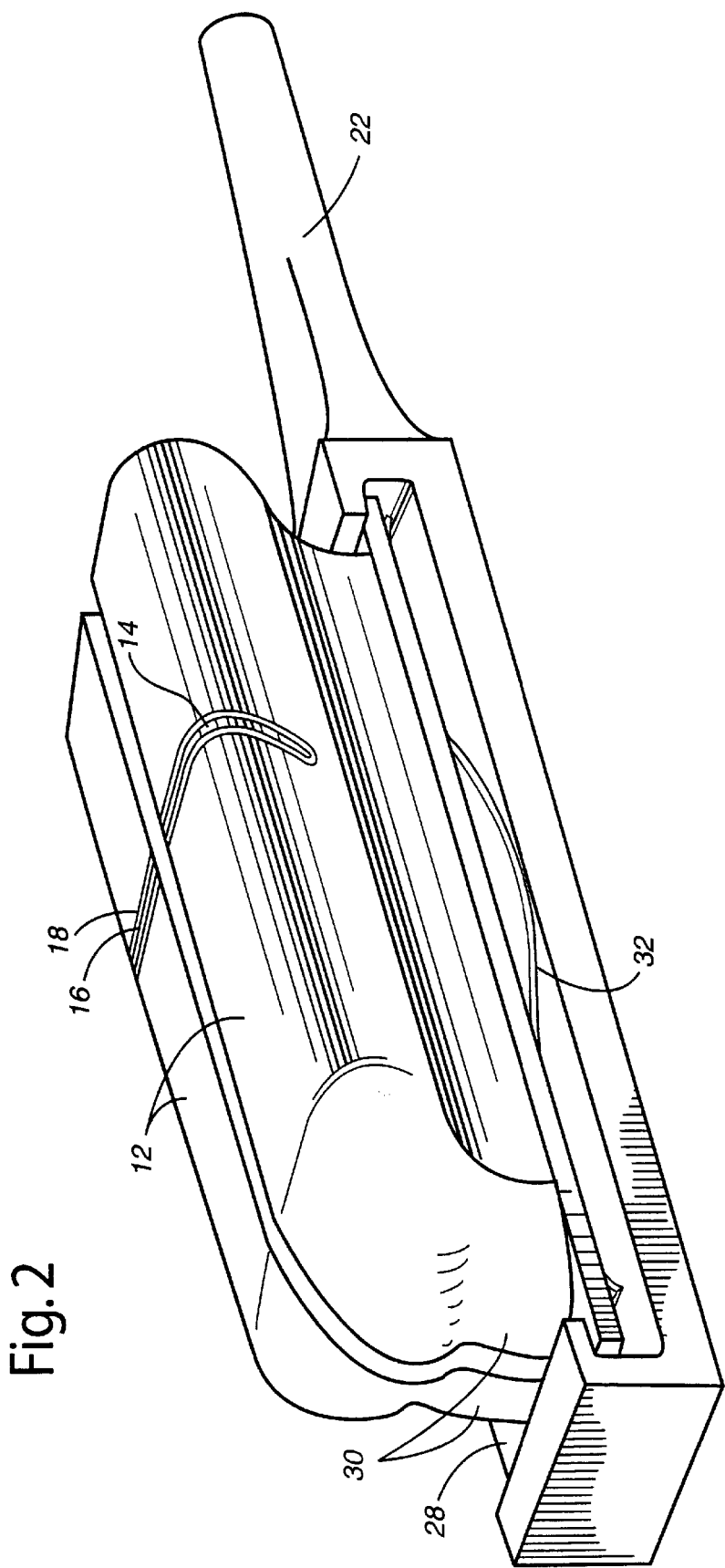
FIG. 2 is a perspective view of a part-specific probe according to the invention.

FIG. 2 is a perspective view of a part-specific probe according to the present invention. In this arrangement, the housing block 12 is shaped corresponding to the contour of a turbine dovetail. This enables the coil to be shaped consistent with the shape of the component to be inspected and thus held in consistent and close proximity to the component surface. It also ensures repeatable positioning of the coils relative to the component. This repeatable and close proximity of the coil to the part surface is essential to ensuring that the eddy currents are consistently induced in the component and that the receive coils are able to detect changes in those eddy currents. Both of these elements are important for sensitive and repeatable inspections.

Figure 2A:
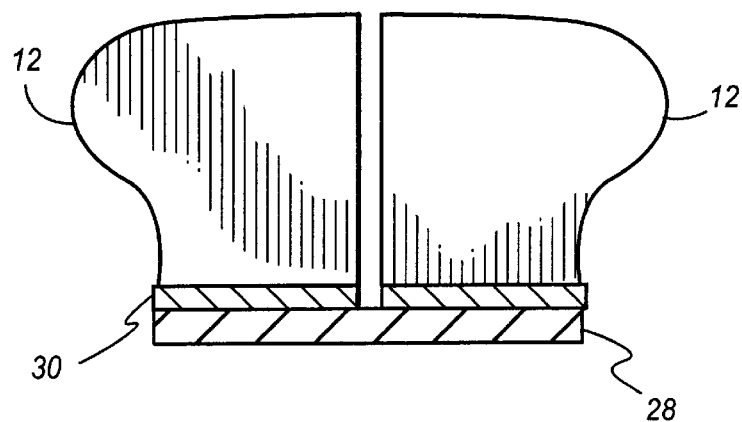
Figure 2B:
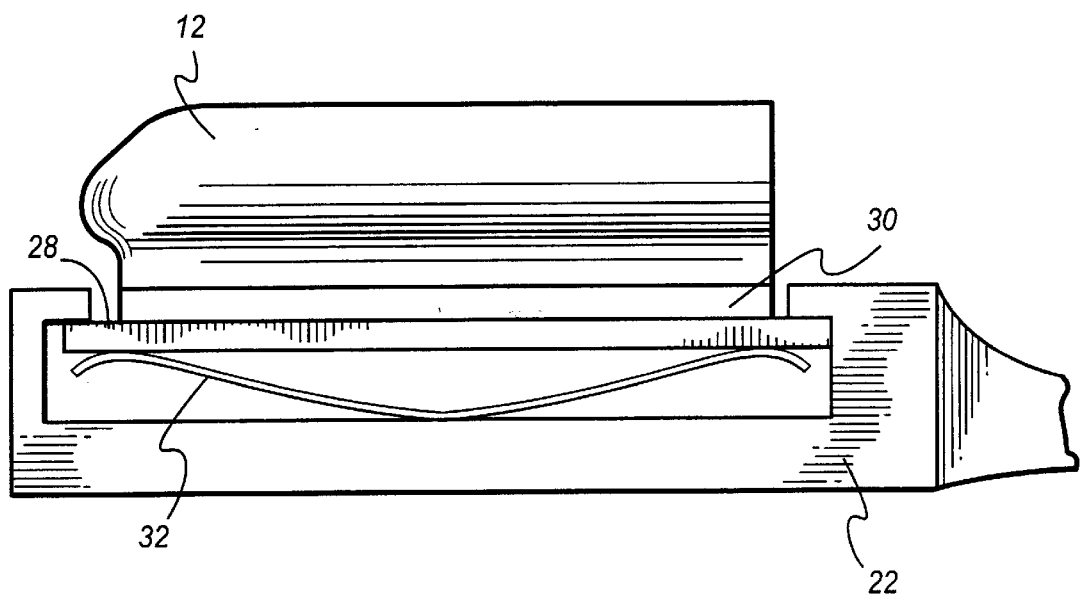

The block 12 is split in half axially to allow for part-to-part tolerances. That is, the split block provides a compliance to the housing, allowing it to conform to the precise dimensions of the part to be inspected. FIGS. 2A and 2B illustrate the details of the mounting of the coil housing block onto the probe stem. FIG. 2A shows the attachment of the block halves to a mounting plate 28. Each half of the block is mounted on an RTV (room temperature vulcanizing) pad 30 that is thick enough and soft enough to flex, allowing some adjustment of the spacing between the two probe halves to accommodate part-to-part dimensional differences. FIG. 2B illustrates the attachment of the mounting plate to the probe stem. The springs 32 shown allow some translation of the mounting plate toward the probe stem, or limited rotation of the mounting plate around or along the stem axis to ensure precise alignment of the coils relative to the component.

Figure 3:
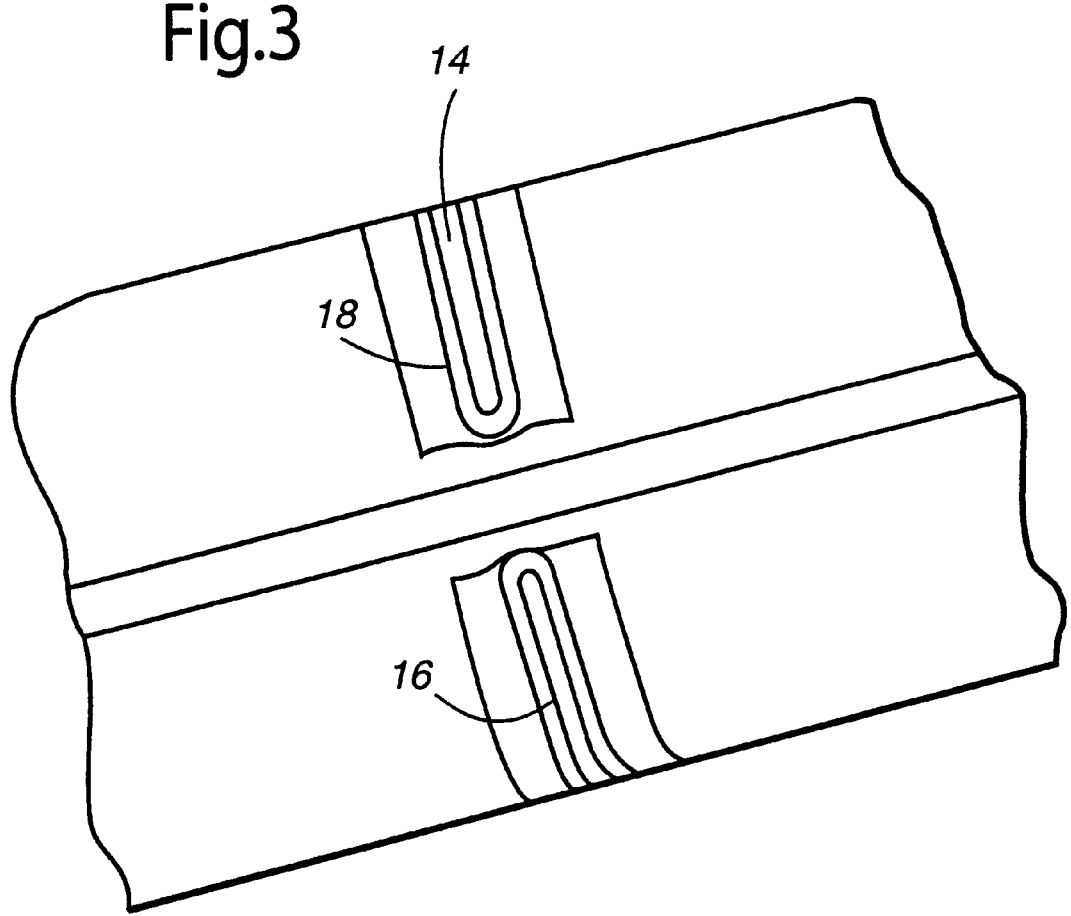
FIG. 3 is a close-up view of the coils in the arrangement shown in FIG. 2.

As shown in FIGS. 2 and 3, one receive coil 16 surrounding a ferrite core 14, and one transmit coil 18 are mounted in each half of the housing 12, allowing both sides of the dovetail slot to be inspected in the same pass of the probe through the slot. In the arrangement illustrated in FIG. 2, the coils 16, 18 themselves and the ferrite cores 14 are shaped to match the contour of the dovetail slot.

With the structure according to the invention, inspection of surfaces such as dovetails can be completed much more quickly. With a conventional coil, the probe must be scanned repetitively along the dovetail slot indexing the probe 0.01" for each pass to assure complete coverage. The time to make these separate passes with the time required to position the probe in the slot results in inspection times exceeding 15 hours. With the probe according to the present invention, the same alignment precision is not required by virtue of the active width of the coils, and further, the probe can complete a dovetail inspection in a single pass. Consequently, inspection time can be reduced to approximately one hour, even including calibration and set-up time.

Figure 4:
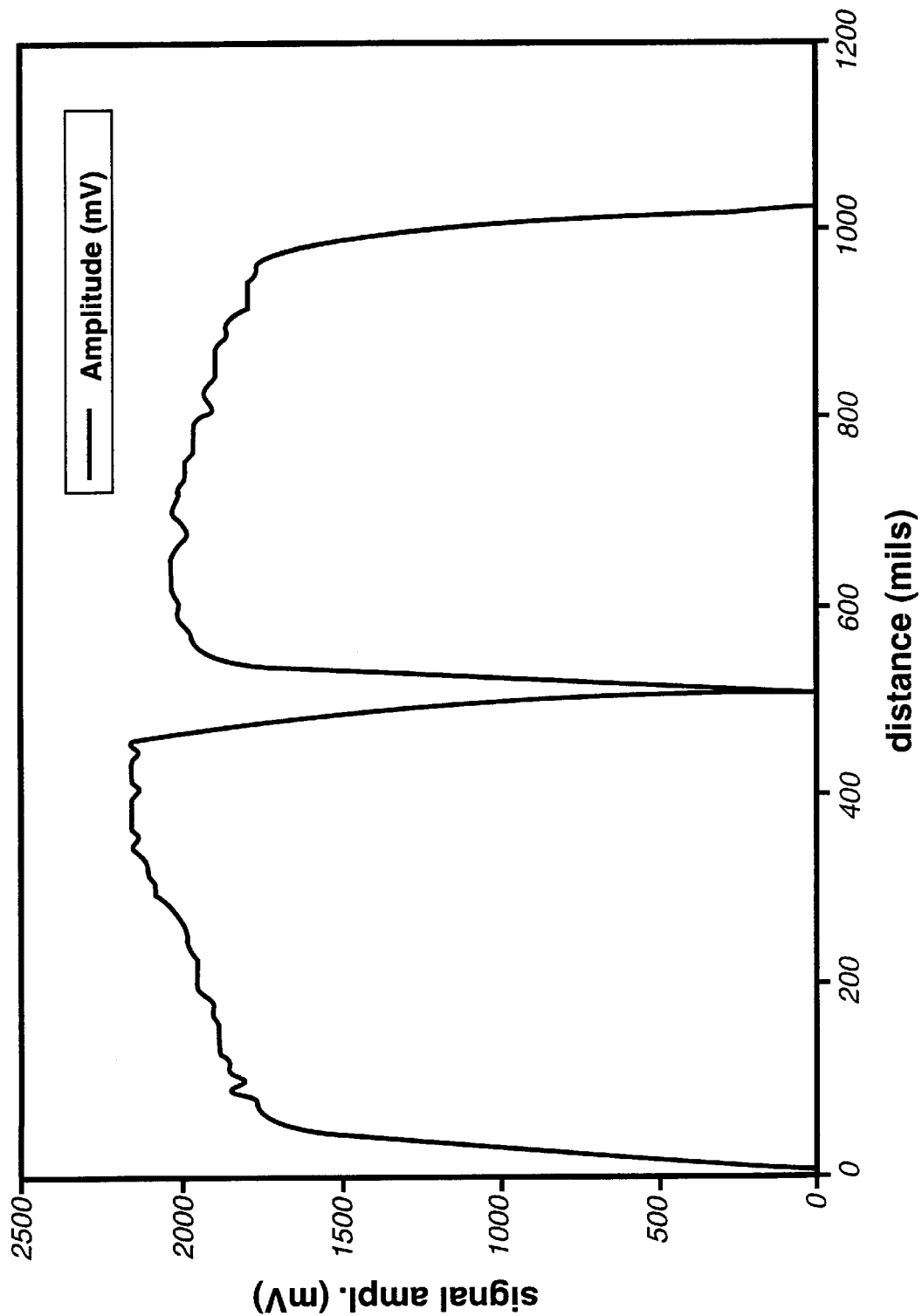
FIG. 4 is a signal amplitude graph illustrating the active width of the coils according to the invention.

FIG. 4 illustrates an exemplary signal amplitude generated from an EDM (electrical discharge machinery) notch as a function of probe position along the coil. The plot was generated using the eddy current probe configured according to the present invention. Signal amplitudes are recorded in millivolts, and the "distance" or "position" of the coil relative to the notch is plotted as the independent variable on the horizontal axis in thousandths of an inch (mils). While the absolute signal is a function of calibration parameters, block material, and of notch dimensions, the relative value of amplitude as a function of relative position of the probe is significant. As shown in FIG. 4, the active width of each of the two receive coils 16 is close to 0.4". That a relatively constant signal obtained for the central 0.4" of each of the two coils is an indicator that the sensitivity of the probe is acceptable for that entire span (approximately 0.8" for the probe). Use of the probe will require some signal processing to recognize the signals generated by the end of the dovetail slot, but such software has been previously developed. The probe according to the invention can be used with conventional instrumentation and equipment already in place in manufacturing and overhaul facilities.

Potential alternatives can be contemplated based on the generation of multiple coil arrays, replacing each pass of the probe according to the invention through the dovetail with a separate coil mounted on a single probe. Although this alternative offers the same inspection throughput benefits as the preferred embodiment of the invention, with no decrease in inspection sensitivity, additional instrumentation (such as multiplexing and different probe drivers) is required as well as a more sophisticated and time-consuming signal processing routine.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An eddy current probe comprising:
   a housing block;
   a pair of elongated ferrite cores disposed end-to-end in the housing block along respective longitudinal axes;
   a pair of receive coils disposed in the housing block respectively surrounding the elongated ferrite cores;
   a transmit coil wound around the receive coils in the housing block; and
   a pair of ferrite shields disposed in the housing block, the ferrite shields sandwiching the transmit coil, the pair of receive coils and the pair of elongated ferrite cores.

2. An eddy current probe according to claim 1, further comprising a probe stem attached to the housing block and a probe electrical connector coupled with a data processing device.

3. An eddy current probe according to claim 1, wherein an active length of each of the pair of receive coils is between 0.2" and 0.6".

4. An eddy current probe according to claim 1, wherein the active length of each of the pair of receive coils is about 0.4".

5. An eddy current probe according to claim 1, wherein the housing block is shaped corresponding to a contour of a turbine dovetail.

6. An eddy current probe according to claim 5, wherein the housing block is split axially.

7. An eddy current probe according to claim 6, wherein one of the pair of receive coils is mounted in each half of the housing block.

8. An eddy current probe according to claim 7, wherein the pair of elongated ferrite cores and the pair of receive coils are shaped corresponding to a turbine dovetail.

9. An eddy current probe according to claim 5, wherein an active length of each of the pair of receive coils is sufficient to complete a turbine dovetail scan in no more than two passes.

10. An eddy current probe according to claim 5, wherein the active length of each of the pair of receive coils is sufficient to complete a turbine dovetail scan in a single pass.

* * * * *